United States Patent
Rane et al.

(10) Patent No.: US 10,118,912 B2
(45) Date of Patent: Nov. 6, 2018

(54) PROCESS FOR THE PREPARATION OF LEDIPASVIR

(71) Applicant: Optimus Drugs Private Ltd., Hyderabad, Telegana (IN)

(72) Inventors: Dnyandev Ragho Rane, Hyderabad (IN); Srinivas Reddy Desi Reddy, Hyderabad (IN); Subbareddy Peketi, Mansurabad (IN); Srinivas Rao Velivela, Hyderabad (IN)

(73) Assignee: Optimus Drugs Private Ltd., Hyderabad (IN)

(*) Notice: Subject to any disclaimer, the term of this patent is extended or adjusted under 35 U.S.C. 154(b) by 0 days.

(21) Appl. No.: 15/196,248

(22) Filed: Jun. 29, 2016

(65) Prior Publication Data

US 2017/0197944 A1    Jul. 13, 2017

(30) Foreign Application Priority Data

Oct. 26, 2015 (IN) .......................... 5716/CHE/2015

(51) Int. Cl.
  *C07D 403/14*   (2006.01)
  *C07D 471/08*   (2006.01)
(52) U.S. Cl.
  CPC ......... *C07D 403/14* (2013.01); *C07D 471/08* (2013.01)

(58) Field of Classification Search
  CPC .................................................. C07D 403/14
  See application file for complete search history.

(56) References Cited

U.S. PATENT DOCUMENTS

| 8,088,368 | B2 | 1/2012 | Guo et al. |
| 9,056,860 | B2 | 6/2015 | Scott et al. |
| 2013/0324496 | A1 | 12/2013 | Scott et al. |
| 2013/0324740 | A1* | 12/2013 | Scott ..................... C07D 403/04 548/300.7 |

FOREIGN PATENT DOCUMENTS

| CN | 104530016 A | 4/2015 |
| WO | 2010132601 A1 | 11/2010 |
| WO | 2013184698 A1 | 12/2013 |
| WO | 2013184702 A1 | 12/2013 |

* cited by examiner

*Primary Examiner* — Laura L Stockton
(74) *Attorney, Agent, or Firm* — Winthrop & Weinstine, P.A.

(57) ABSTRACT

An improved process is provided for the preparation of Ledipasvir and its pharmaceutically acceptable salts or solvates thereof, which is useful as an antiviral agent. This disclosure also provides a process for the preparation of key intermediates of Ledipasvir.

2 Claims, No Drawings

PROCESS FOR THE PREPARATION OF LEDIPASVIR

I. BACKGROUND OF THE INVENTION

A. Field of Invention

The present invention provides an improved process for the preparation of the compound of formula I and its pharmaceutically acceptable salts or solvates thereof, which is useful as an antiviral agent.

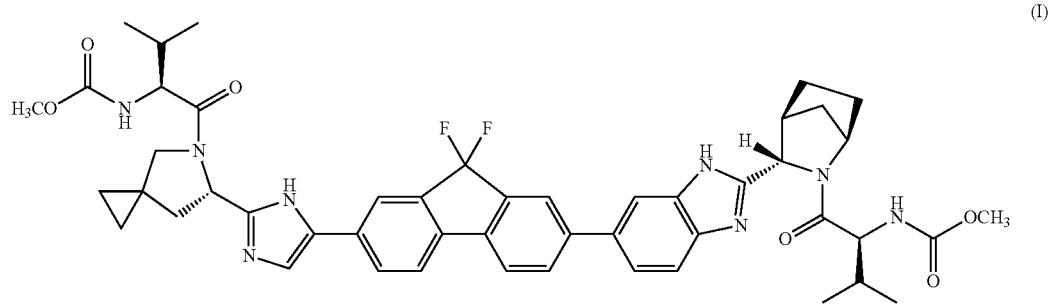 [SMILES: COC(=O)N[C@H](C(=O)N1CC2(CC2)C[C@H]1c1ncc(-c2ccc3c(c2)C(F)(F)c2cc(-c4ccc5nc([C@@H]6[C@H]7CC[C@H](C7)N6C(=O)[C@@H](NC(=O)OC)C(C)C)[nH]c5c4)ccc2-3)[nH]1)C(C)C]

B. Description of the Related Art

Ledipasvir is chemically known as Methyl [(2S)-1-{(6S)-6-[5-(9,9-difluoro-7{2-[(1R,3S,4S)-2-{(2S)-2-[(methoxycarbonyl)amino]-3-methylbutanoyl}-2azabicyclo[2.2.1]hept-3-yl]-1H-benzimidazol-6-yl)}-9H-fluoren-2-yl)-1H-imidazol-2-yl]-5azaspiro[2.4]hept-5-yl}-3-methyl-1-oxobutan-2-yl]carbamate. Ledipasvir is a hepatitis C virus (HCV) NS5A inhibitor. Ledipasvir is indicated for the treatment of chronic hepatitis C (CHC) genotype 1 infection in adults (1) and it is marketed under the brand name HARVONI®.

The present disclosure relates generally to the field of an improved process for the preparation of formula (I). Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

Ledipasvir and its pharmaceutical acceptable salts are first disclosed in U.S. Pat. No. 8,088,368 B2, and its process for the preparation discloses as 2,7-dibromo-fluoren-9-one (II) is reacted with deoxofluor to produce 2,7-dibromo-9,9-difluoro-9H-fluorene (III). The compound of formula (III) is condensed with N-Cbz-4-cyclopropyl (L) proline in presence of Pd catalyst and ethoxyvinyltributyl tin and DIEA to produce the compound of formula (IV). The compound of formula (IV) is cyclized in presence of m-xylene/ammonium acetate to produce the compound of formula (V), Further it is condensed with 2-(L)-methoxycarbonylamino-3-butyric acid (VI) in presence of DIEA in HATU and solvent to produce the compound of formula (VII). The compound of formula (VII) is condensed with compound of formula (VIII) in presence of Pd catalyst and base to produce the compound of formula (IX). Finally the compound of formula (IX) is coupled with methoxy carbonyl L-valine of formula (VI) in presence of DIEA in HATU and solvent to produce the compound of formula (I).

The above process is schematically as shown in below:

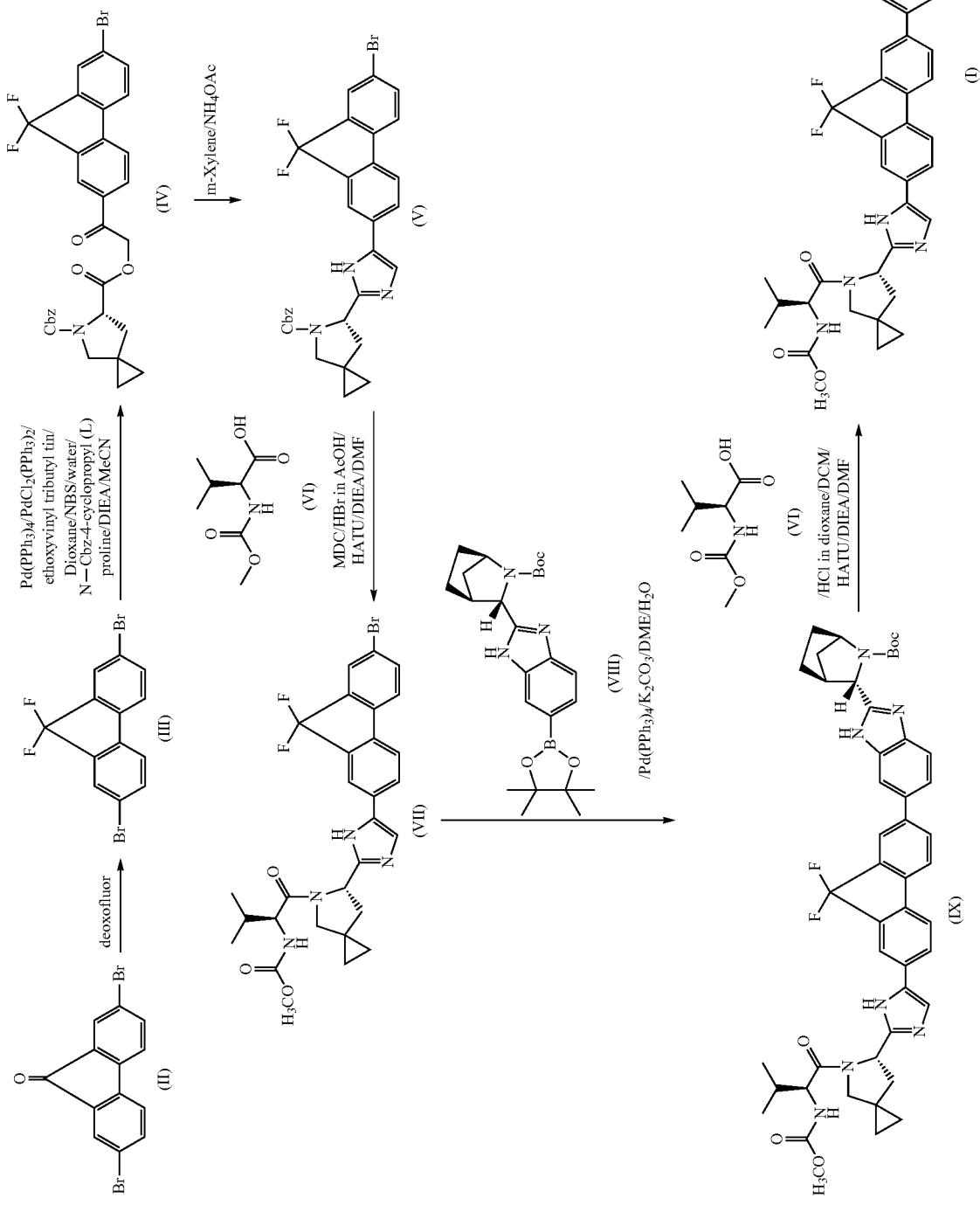

U.S. Pat. No. 9,056,860 B2 also discloses a process for the preparation of the compound of formula (I) comprising the step of condensing the compound of formula (V) with the compound of formula (VIII) in presence of $PdCl_2 [P(t-Bu)_2Ph]_2$ or palladium acetate and base to produce the compound of formula (III), followed by deprotection to produce the compound of formula (IV). Finally the compound of formula (IV) is coupled with carbonyl L-valine of formula (VI) to produce the compound of formula (I).

The above process is schematically as shown in below

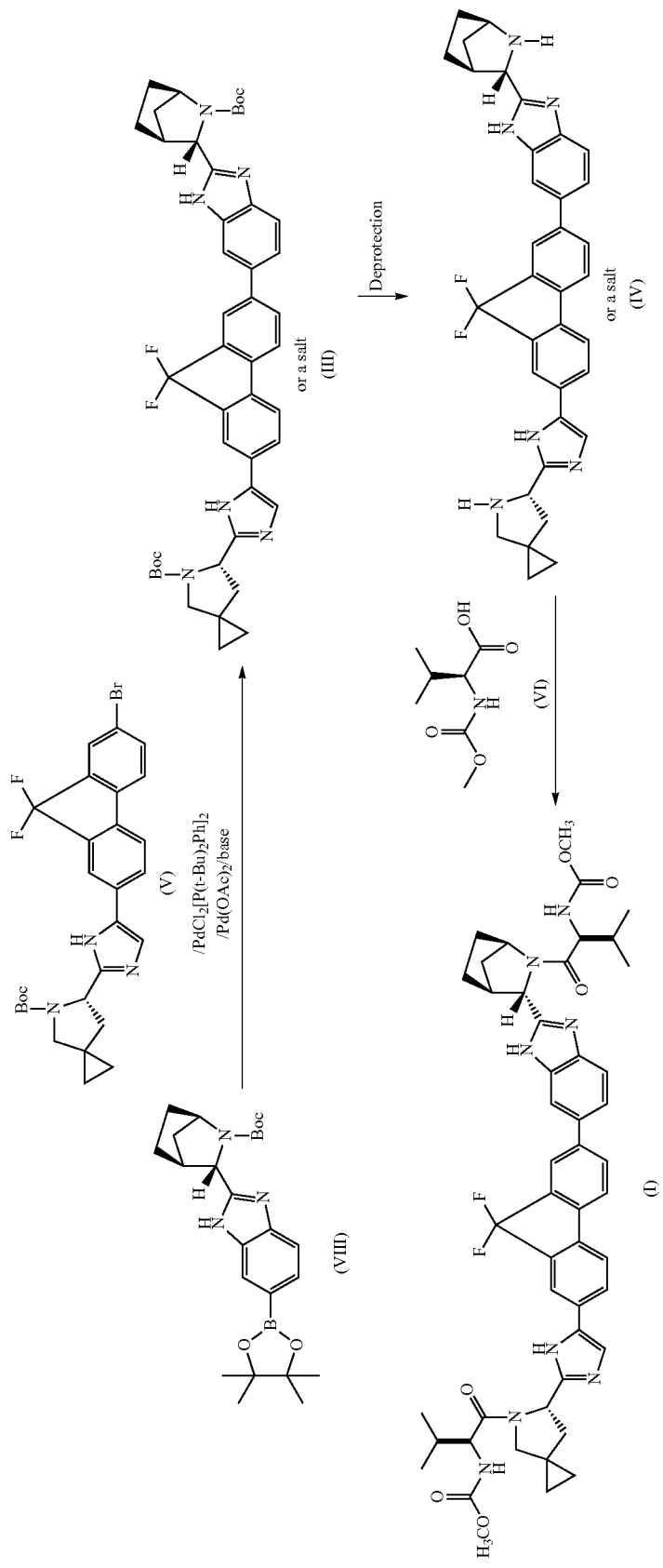

WO 2013/184698 A1 discloses amorphous and various crystalline forms of the compound of formula (I) and its salts or solvates thereof. This disclosure also provides a process for the preparation of making the amorphous form and crystalline forms and methods for using them in the treatment of HCV.

The major disadvantage with the above prior art process is its use of expensive catalysts and large amounts of solvents. Additionally, the yield of the prior art process is diminished by the large amount of by-products and impurities. Therefore, the prior art process for preparing Ledipasvir is not optimal for industrial scale production.

Hence, there is consequently a need for an improved method for the preparation of Ledipasvir and its intermediates which does not involve the problems described above. Some embodiments of the present invention may provide one or more benefits or advantages over the prior art.

II. SUMMARY OF THE INVENTION

The present invention provides an improved process for the preparation of compounds of formula I and it also provides an industrially feasible, commercially viable, and eco-friendly process for the preparation of Ledipasvir.

One aspect of the present invention is to provide an improved process for the preparation of Ledipasvir having formula (I) and its salts comprising the steps of:

a. reacting (1R,3S,4S)-3-(6-bromo-1H-benzimidazol-2-yl)-2-azabicyclo[2.2.1]heptane-2-carboxylic acid 1,1-dimethylethyl ester of formula (X) with bis(pinacolato)diboron in the presence of base/Pd or Ni catalyst and solvent to produce (1R,3S,4S)-3-[6-(4,4,5,5-tetramethyl-1,3,2-dioxaborolan-2-yl)-1H-benzimidazol-2-yl]-2-azabicyclo[2.2.1]heptane-2-carboxylic acid 1,1-dimethylethyl ester (VIII),

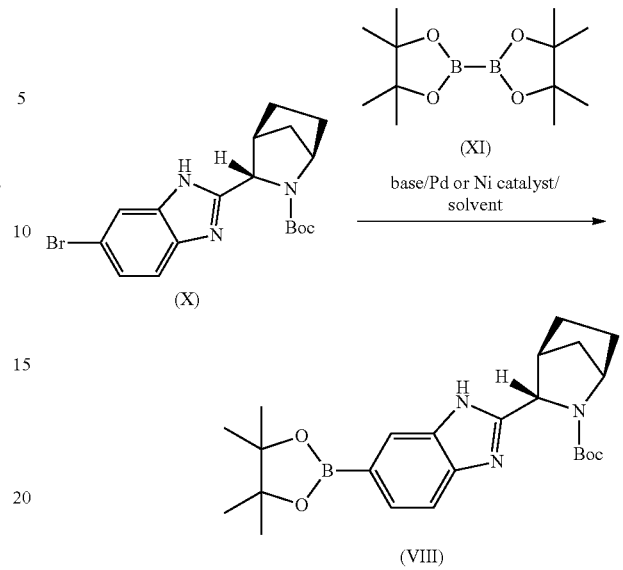

wherein Pd or Ni catalyst is selected from dichloro bis(di-tert-butylphenylphosphine) palladium (II) or dichloro bis(di-tert-butylphenylphosphine) nickel (II);

b. condensing (1R,3S,4S)-3-[6-(4,4,5,5-tetramethyl-1,3,2-dioxaborolan-2-yl)-1H-benz imidazol-2-yl]-2-azabicyclo[2.2.1]heptane-2-carboxylic acid 1,1-dimethylethyl ester of formula (VIII) with (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester of Formula (V) in presence of Pd or Ni catalyst and solvent; optionally using triphenyl phosphine (TPP) under argon atmosphere to produce (1R,3S,4S)-tert-butyl 3-(6-(7-(2-((S)-5-(tert-butoxycarbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III),

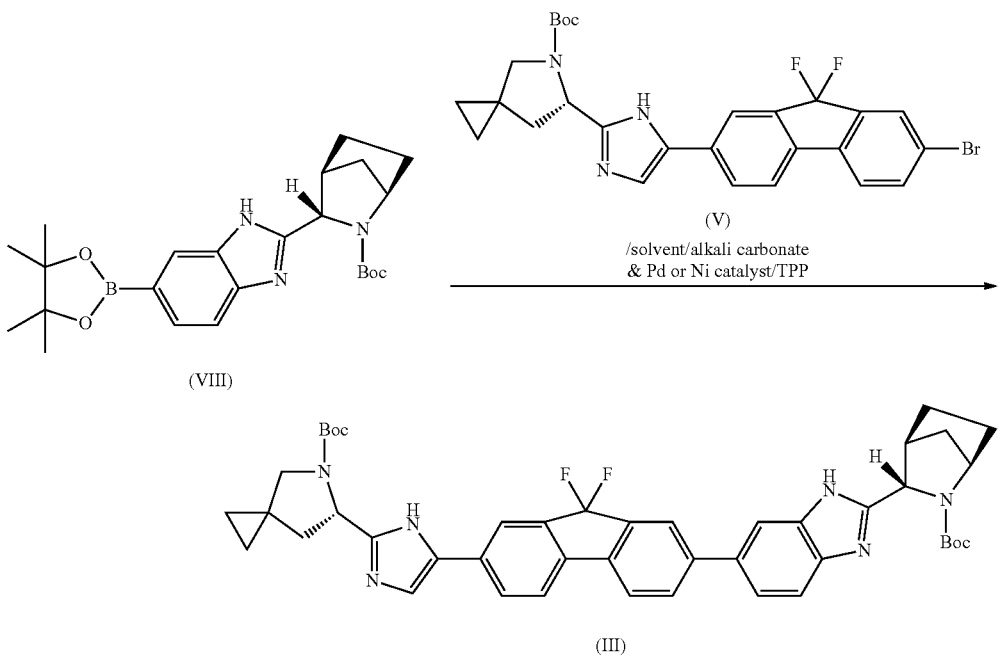

wherein the Pd or Ni catalyst is selected from dichloro bis triphenyl phosphene palladium (II) or dichloro bis triphenyl phosphene nickel (II);

c. deprotecting (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III) in the presence of acid to produce 6-(7-(2-((S)-5-azaspiro[2.4]heptan-6-yl)-1H-imidazol-5-yl)-9,9-difluoro-9H-fluoren-2-yl)-2-((1R,3S,4S)-2-azabicyclo[2.2.1]heptan-3-yl)-1H-benzo[d]imidazole, free base of formula (IV);

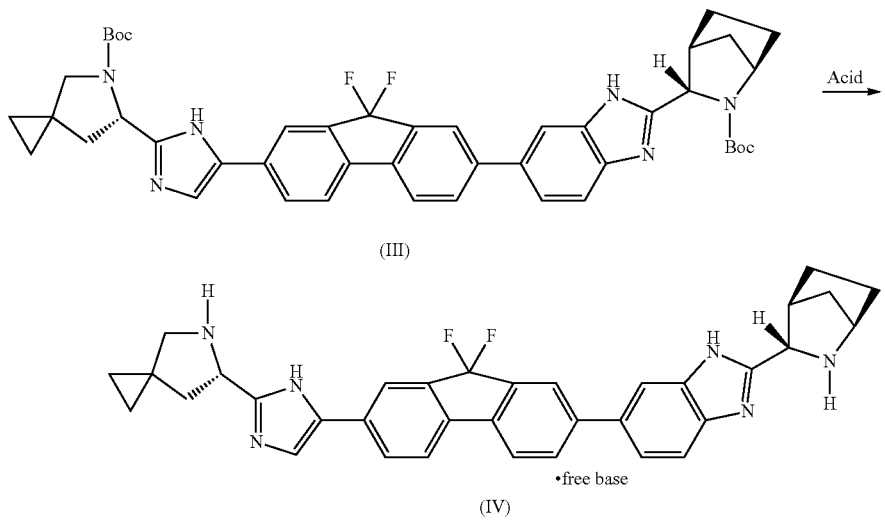

d. coupling the compound of formula (IV) with methoxy carbonyl L-valine of formula (VI) in the presence of HOBT/EDC.HCl (or) HATU/EDC.HCl and base to produce Ledipasvir having formula (I).

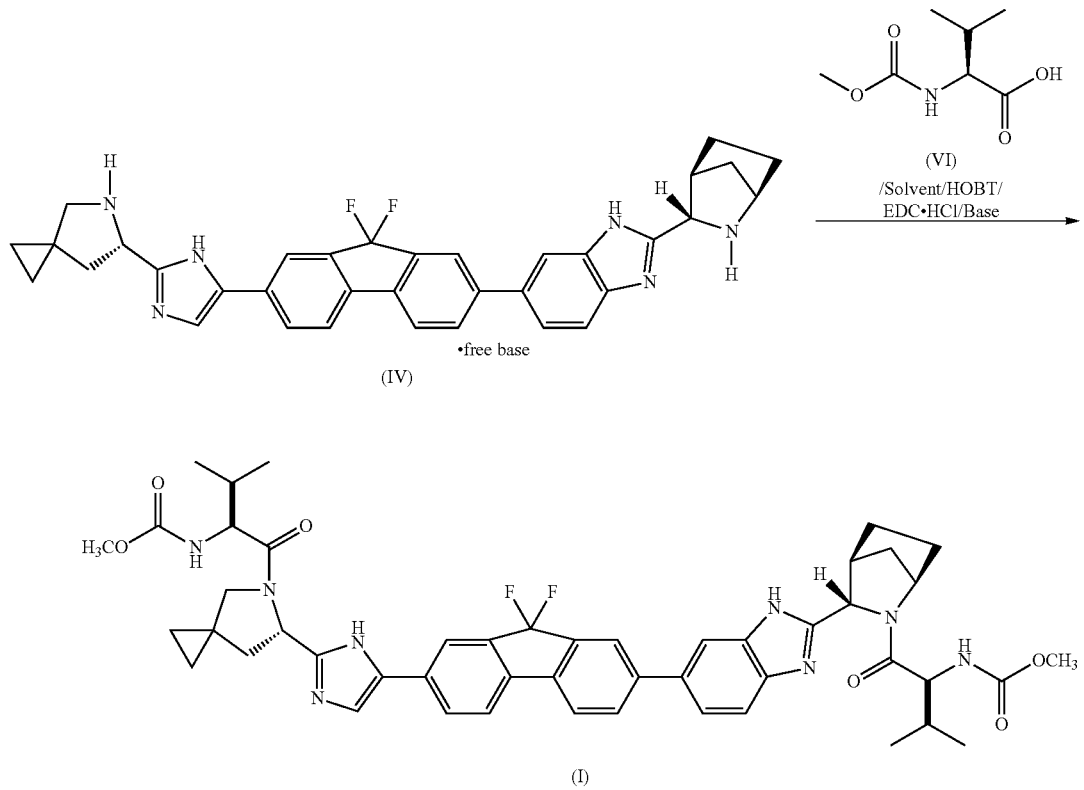

Another aspect of the present invention also provides an improved process for the preparation of compounds of formula (III) by novel catalysts including the step of:

condensing (1R,3S,4S)-3-[6-(4,4,5,5-tetramethyl-1,3,2-dioxaborolan-2-yl)-1H-benz imidazol-2-yl]-2-azabicyclo [2.2.1]heptane-2-carboxylic acid 1,1-dimethylethyl ester of formula (VIII) with (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester of formula (V) in the presence of palladium or nickel catalyst/solvent; optionally using triphenyl phosphine (TPP) under argon atmosphere to produce (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III), that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not necessarily require every element of a list or only one element of a list to the exclusion of others.

Embodiments of the present invention may provide an improved, cost-effective and eco-friendly process for the preparation of Ledipasvir (I) in good yield with high purity.

In one embodiment of the present invention includes the step of reacting (1R,3S,4S)-3-(6-bromo-1H-benzimidazol-

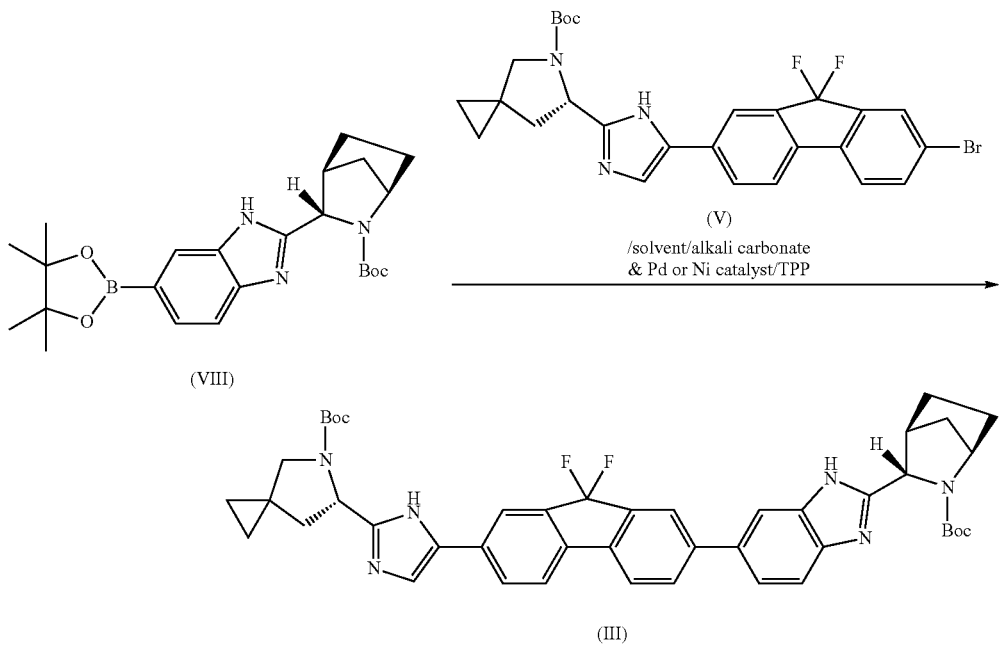

wherein the Pd or Ni catalyst is selected from dichloro bis triphenyl phosphene palladium (II) or dichloro bis triphenyl phosphene nickel (II).

Another aspect of the present invention provides a process for the preparation of Ledipasvir acetone solvate and further converts it into amorphous form.

Other benefits and advantages will become apparent to those skilled in the art to which it pertains upon reading and understanding of the following detailed specification.

III. DETAILED DESCRIPTION OF THE INVENTION

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate 2-yl)-2-azabicyclo[2.2.1]heptane-2-carboxylic acid 1,1-dimethylethyl ester of formula (X) with bis(pinacolato)diboron in the presence of base/Pd or Ni catalyst and solvent to produce (1R,3S,4S)-3-[6-(4,4,5,5-tetramethyl-1,3,2-dioxaborolan-2-yl)-1H-benzimid Furthermore the Pd or Ni catalyst may be selected from dichloro bis (di-tert-butylphenylphosphine) palladium (II) or dichloro bis (di-tertbutylphenylphosphine) nickel (II). azol-2-yl]-2-azabicyclo [2.2.1]heptane-2-carboxylic acid 1,1-dimethylethyl ester (VIII).

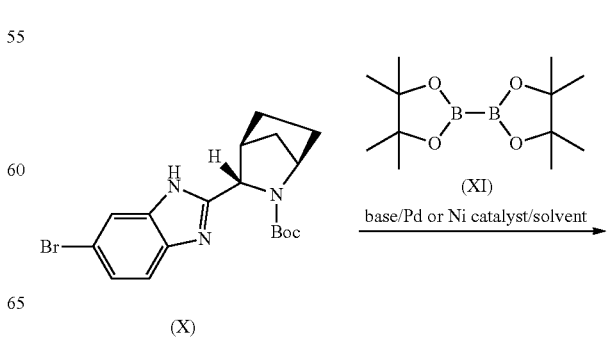

-continued

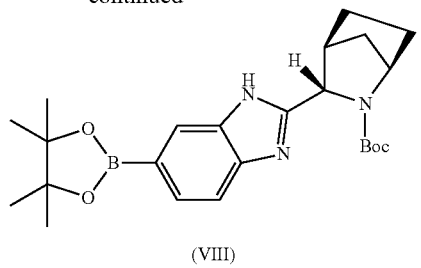

(VIII)

Embodiments may further include condensing (1R,3S,4S)-3-[6-(4,4,5,5-tetramethyl-1,3,2-dioxaborolan-2-yl)-1H-benz imidazol-2-yl]-2-azabicyclo[2.2.1]heptane-2-carboxylic acid 1,1-dimethylethyl ester of formula (VIII) with (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester of formula (V) in presence of palladium or nickel catalyst/solvent, and optionally using triphenyl phosphine (TPP) under argon atmosphere to produce (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III). Furthermore, the Pd or Ni catalyst selected from dichloro bis triphenyl phosphene palladium (II) or dichloro bis triphenyl phosphene nickel (II).

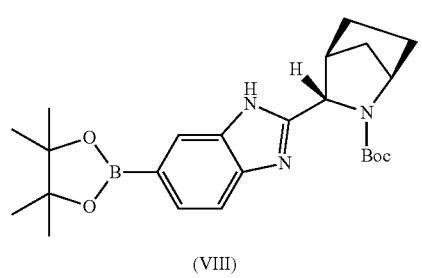

(VIII)

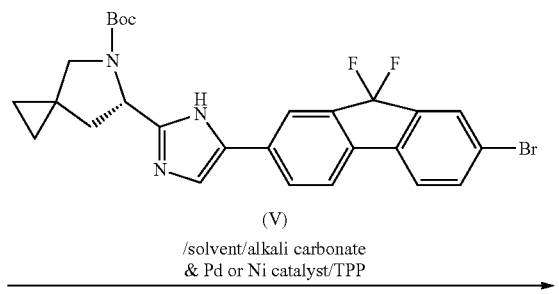

(V)

/solvent/alkali carbonate
& Pd or Ni catalyst/TPP
→

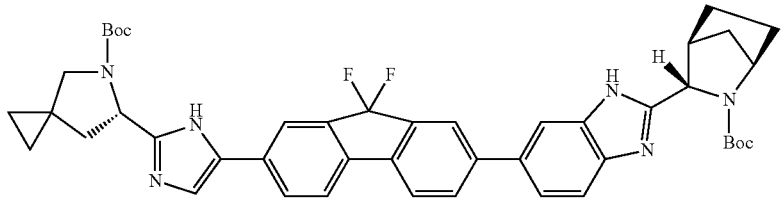

(III)

Embodiments may further include the step of deprotecting (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III) in the presence of acid to produce 6-(7-(2-((S)-5-azaspiro[2.4]heptan-6-yl)-1H-imidazol-5-yl)-9,9-difluoro-9H-fluoren-2-yl)-2-((1R,3S,4 S)-2-azabicyclo[2.2.1]heptan-3-yl)-1H-benzo[d]imidazole, free base of formula (IV).

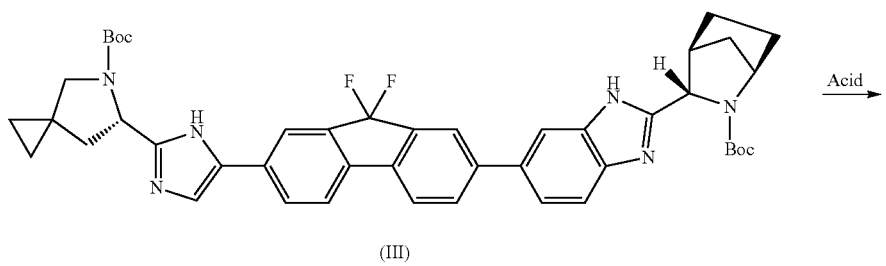

(III)

Acid →

-continued

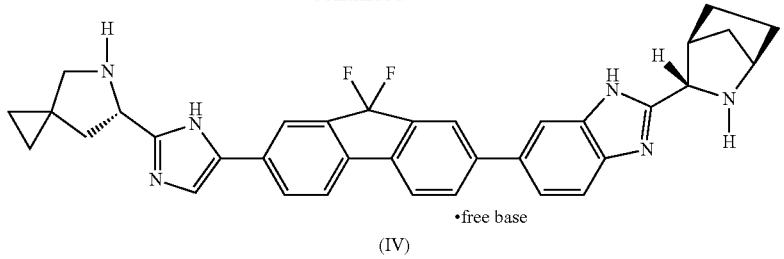

(IV)

According to some embodiments, the process may further include coupling the compound of formula (IV) with methoxy carbonyl L-valine of formula (VI) in presence of HOBT/EDC.HCl (or) HATU/EDC.HCl and base to produce Ledipasvir (I).

Another embodiment of the present invention may provide an improved process for the preparation of the compound of formula (III) by novel catalysts. A first step in the process may include condensing (1R,3S,4S)-3-[6-(4,4,5,5-tetramethyl-1,3,2-dioxaborolan-2-yl)-1H-benz imidazol-2-yl]-2-azabicyclo[2.2.1]heptane-2-carboxylic acid 1,1-dimethylethyl ester of formula (VIII) with (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester of formula (V) in the presence of palladium or nickel catalyst, and solvent. Optionally, triphenyl phosphine (TPP) may be used under argon atmosphere to produce (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III). Furthermore, the Pd or Ni catalyst may be selected from dichloro bis triphenyl phosphene palladium (II) or dichloro bis triphenyl phosphene nickel (II).

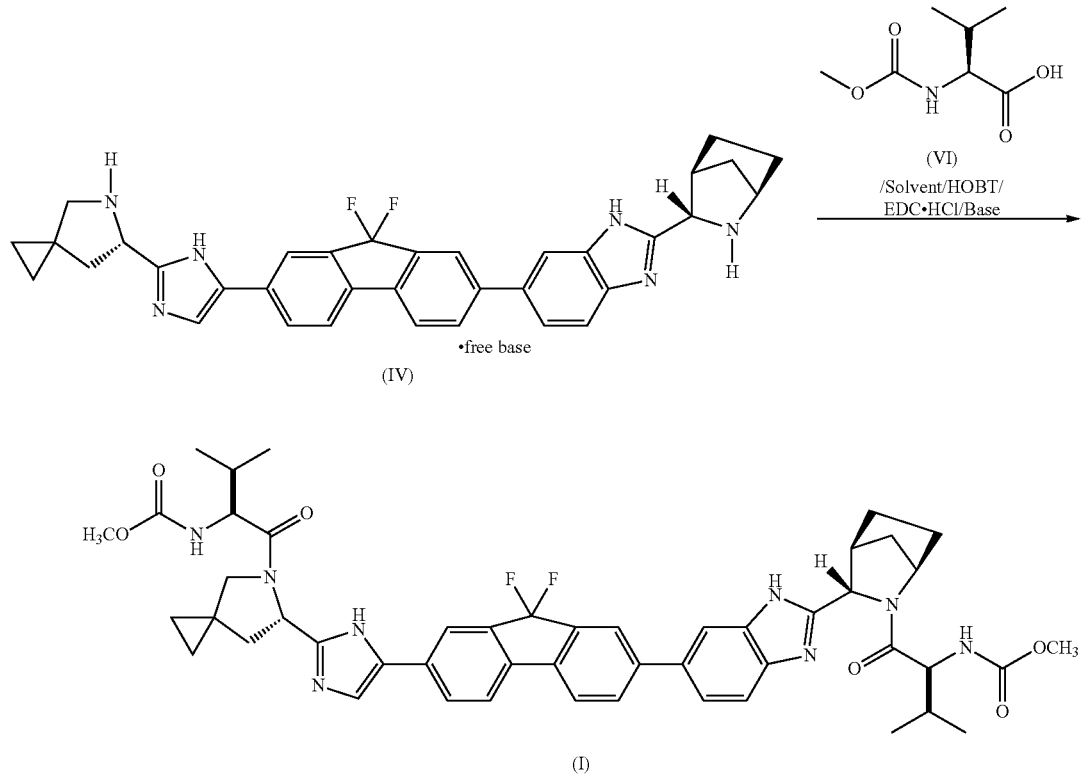

According to an embodiment of present invention, the compound of formula (X) may be reacted with bis (pinacolato) diboron of formula (XI) in presence of base, Pd or Ni catalyst, and solvent to produce the compound of formula (VIII). The compound of formula (VIII) is then condensed with the compound of formula (V) in presence of dichloro bis triphenyl phosphene palladium (II) or dichloro bis triphenyl phosphene nickel (II), and solvent. Optionally, triphenyl phosphine (TPP) may be used under argon atmosphere to produce the compound of formula (III); followed by deprotecting in the presence of acid to produce the free base compound of formula (IV). Finally, the process may include coupling of the compound of formula (IV) with methoxy carbonyl L-valine of formula (VI) in the presence of HOBT/EDC.HCl (or) HATU/EDC.HCl and base to produce Ledipasvir (I).

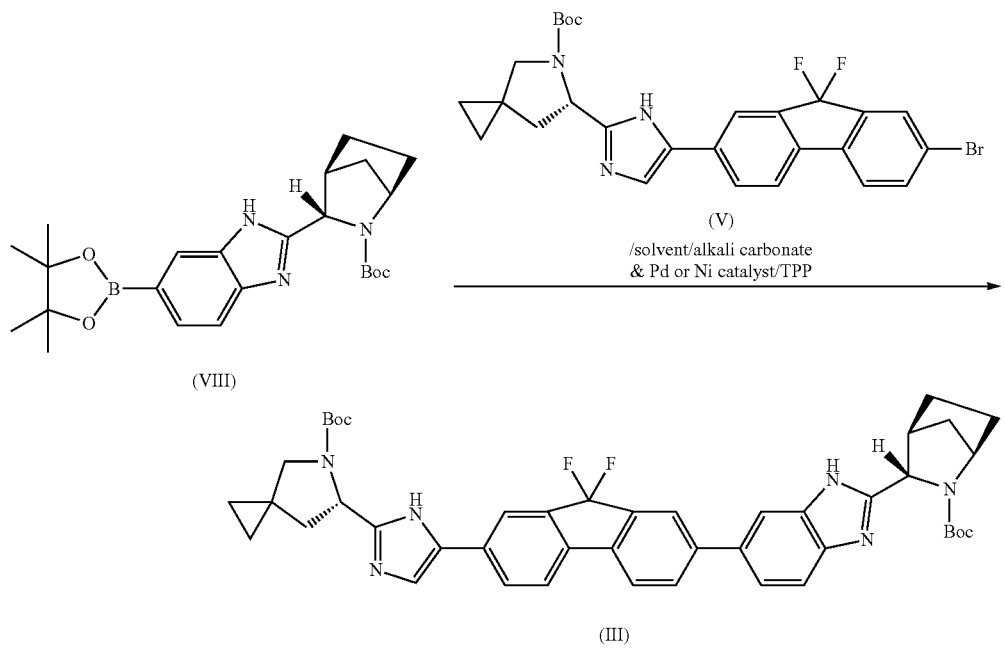

(VIII)

(V)

/solvent/alkali carbonate
& Pd or Ni catalyst/TPP (III)

According to another embodiment of the present invention, the solvent may selected from dimethyl formamide, 1,4-dioxane, ethanol, methanol, dichloromethane (DCM), tetrahydrofuran (THF), ethylacetate, acetone and water. The alkali carbonate may selected from sodium carbonate, potassium carbonate, lithium carbonate. The base may be selected from sodium hydroxide, potassium hydroxide, lithium hydroxide, sodium propionate, potassium propionate, sodium acetate, potassium acetate, lithium propionate, methyl amine, ethyl amine, N,N-diisopropyl ethyl amine, aniline. The catalyst may be selected from palladium acetate, tetrakis triphenyl phosphene palladium (II), dichloro bis(di-tert-butylphenylphosphine)palladium (II), dichloro bis triphenyl phosphene palladium (II), dichloro[1,1'-bis(diphenylphosphino)ferrocene]palladium(II), bis[di-tert-butyl(4-dimethylaminophenyl)phosphino]palladium(II) chloride, bis[di-(tert-butyl(4-dimethylaminophenyl)phosphino] palladium (II) chloride, and bis[di-(tert-butyl)(4-fluoromethylphenyl)phosphine]palladium(II) chloride. The nickel catalyst may be selected from tetrakis triphenyl phosphene nickel (II), dichloro bis(di-tert-butylphenylphosphine)nickel (II), dichloro bis triphenyl phosphene nickel (II), dichloro[1,1'-bis(diphenylphosphino)ferrocene]nickel (II), bis[di-tert-butyl(4-dimethylaminophenyl)phosphino] nickel(II) chloride, bis[di-(tert-butyl(4-dimethylaminophenyl)phosphino]nickel (II) chloride, and bis[di-(tert-butyl)(4-fluoromethylphenyl)phosphine]nickel(II) chloride. The acid may be selected from hydrochloric acid, sulfuric acid, nitric acid, phosphoric acid, carbonic acid, hydro sulfuric acid, acetic acid, and trifluoroacetic acid. Coupling agents may be selected from HOBT/EDC.HCl, or HATU/EDC.HCl. The phosphine may be selected from triphenylphosphine, tri(2-methoxyphenyl)phosphine, tricyclohexylphosphine, 2-(dicyclohexylphosphino)biphenyl, 2-dicyclohexylphosphino-2'-methylbiphenyl, 2-(dicyclohexylphosphino)-2'-(N,N-dimethylamino)biphenyl, 2-(di-tert-butylphosphino)-2'-(N,N-dimethylamino)biphenyl, dicyclohexyl(2,2-diphenyl-1-methylvinyl)phosphine and the like.

In yet another embodiment of the present invention a process is provided for the preparation of Ledipasvir acetone solvate and further converts it into amorphous form.

According embodiments of the present invention, the Ledipasvir may be dissolved in organic solvents like THF, DCM, ethyl acetate, methanol, ethanol, isopropanol, and/or isopropyl acetate and stirred at room temperature. The organic solvent may be evaporated under reduced pressure to yield a residue, followed by acetone to isolate Ledipasvir acetone solvate.

Further Ledipasvir acetone solvate is dissolved in an organic solvent to produce a clear solution. Activated carbon may be added and the mixture may be stirred at 0 to 5° C. and filter through a high flow bed. The obtained filtrate may be stirred and cooled to 0 to 5° C. Optionally, an anti-solvent may be added like water, methyl tertiary butyl ether, hexane, heptane and the like to produce solid precipitate. The resultant solid may be filtered and dried at 70 to 90° C. to obtain Ledipasvir in amorphous form.

Certain process details of particular embodiments of the invention are provided in the example given below, which are provide by way of illustration only and therefore should not be construed to limit the scope of the invention.

EXAMPLES

Example-1: Preparation of (1R,3S,4S)-3-[6-(4,4,5,5-tetramethyl-1,3,2-dioxaborolan-2-yl)-1H-benzimidazol-2-yl]-2-azabicyclo[2.2.1]heptane-2-carboxylic acid 1,1-dimethylethyl ester (1R,3S,4S)-3-(6-bromo-1H-benzimidazol-2-yl)-2-azabicyclo[2.2.1]heptane-2-carboxylic acid 1,1-dimethylethyl ester (25 g) may be suspended in 1,4 dioxane (250 ml), followed by addition of bis(pinacolate) diboron (35.5 g), dichlorobis(di-tert-butylphenylphosphine)palladium(II) catalyst (1.5 g) and potassium acetate (18 g) at room temperature and the temperature may be raised to 80-85° C. for 2-3 hours, or until the reaction goes to completion.

Completion may be confirm by TLC. The 1, 4 dioxane solvent was distilled under reduced pressure and the reaction mass may be cooled to room temperature by adding purified water and dichloromethane to separate the layers. The organic layer was distilled out under reduced pressure to get a residue and it may be further treated with cyclohexane to produce a solid. Finally, the resultant solid was filtered and dried at 40-50° C. to obtain 26 g of the objective compound.

Example-2: Preparation of (1R,3S,4S)-3-[6-(4,4,5,5-tetramethyl-1,3,2-dioxaborolan-2-yl]-1H-benzimidazol-2-yl]-2-azabicyclo[2.2.1]heptane-2-carboxylic acid 1,1-dimethylethyl ester (1R,3S,4S)-3-(6-bromo-1H-benzimidazol-2-yl)-2-azabicyclo[2.2.1]heptane-2-carboxylic acid 1,1-dimethylethyl ester (25 g) may be suspended in dimethylformamide (250 ml), followed by addition of bis(pinacolate) diboron (35.5 g), dichlorobis(di-tert-butylphenylphosphine)nickel(II) catalyst (1.5 g) and sodium acetate (18 g) at room temperature. The temperature may be raised to 80-85° C. for 2-3 hours until the reaction goes to completion. Completion may be confirm by TLC. The dimethylformamide solvent was distilled out under reduced pressure and the reaction mass was cooled to room temperature by adding purified water and dichloromethane, to separate the layers. The organic layer may be distilled out under reduced pressure to produce a residue, and it may be further treated with hexane to produce a solid precipitate. Finally, the resultant solid was filtered and dried over at 40-50° C. to obtain 29 g of the objective compound.

Example-3: Preparation of (1R,3S,4S)-tert-butyl 3-(6-(7-(2-((S)-5-(tert-butoxy carbonyl)-5-azaspiro [2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate 1,4 dioxane (370 ml) and purified water (250 ml) were added to (1R,3S,4S)-3-[6-(4,4,5,5-tetramethyl-1,3,2-dioxaborolan-2-yl)-1H-benzimidazol-2-yl]-2-azabicyclo[2.2.1] heptane-2-carboxylic acid 1,1-dimethylethyl ester (25 g) at room temperature, followed by addition of dimethylformamide (35 ml), sodium carbonate (15 g), (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester (25 g), triphenyl phosphine (1.25 g) and dichloro bis triphenyl phosphine palladium (II) catalyst (0.6 gm) under argon atmosphere at room temperature. The reaction mixture temperature may be raised to 80-85° C. and maintained for 1-3 hours. After completion of reaction (checked by TLC), the solvent may be filtered through a high flow bed and the filtrate was distilled out under reduced pressure and cooled to room temperature, followed by addition of water to isolate the free base solid of the objective compound (25-30 g).

Example-4: Preparation of (1R,3S,4S)-tert-butyl 3-(6-(7-(2-((S)-5-(tert-butoxy carbonyl)-5-azaspiro [2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate Tetrahydrofuran (370 ml) and purified water (250 ml) were added to (1R,3S,4S)-3-[6-(4,4,5,5-tetramethyl-1,3,2-dioxaborolan-2-yl]-1H-benzimidazol-2-yl]-2-azabicyclo [2.2.1]heptane-2-carboxylic acid 1,1-dimethylethyl ester (25 g) at room temperature, followed by addition of sodium carbonate (15 g), (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester (25 g), triphenyl phosphine (1.25 g) and palladium chloride catalyst (0.6 gm) under argon atmosphere at room temperature. The reaction mixture temperature may be raised to 80-85° C. and maintained for 1-3 hours. After completion of the reaction (checked by TLC), the solvent may be filtered through a high flow bed and the filtrate may be distilled out under reduced pressure, cooled to room temperature, followed by addition of water to isolate the free base solid of the objective compound (25-30 g).

Example-5: Preparation of (1R,3S,4S)-tert-butyl 3-(6-(7-(2-((S)-5-(tert-butoxy carbonyl)-5-azaspiro [2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate 1,4 dioxane (370 ml) and purified water (250 ml) were added to (1R,3S,4S)-3-[6-(4,4,5,5-tetramethyl-1,3,2-dioxaborolan-2-yl)-1H-benzimidazol-2-yl]-2-azabicyclo[2.2.1] heptane-2-carboxylic acid 1,1-dimethylethyl ester (25 g) at room temperature, followed by addition of dimethylformamide (35 ml), sodium carbonate (15 g), (6S)-6-[5-(7-bromo-9,9-difluoro-9H-fluoren-2-yl)-1H-imidazol-2-yl]-5-azaspiro[2.4]heptane-5-carboxylic acid 1,1-dimethylethyl ester (25 g), triphenyl phosphine (1.25 g) and dichloro bis triphenyl phosphine nickel (II) catalyst (0.6 gm) under argon atmosphere at room temperature. The reaction mixture temperature may be raised to 80-85° C. and maintained for 1-3 hours. After completion of the reaction (checked by TLC), the solvent may be filtered through a high flow bed and filtrate was distilled out under reduced pressure, cooled to room temperature, followed by addition of water to isolate the free base solid of the objective compound (25-30 g).

Example-6: Preparation of 6-(7-(2-((S)-5-azaspiro [2.4]heptan-6-yl)-1H-imidazol-5-yl)-9,9-difluoro-9H-fluoren-2-yl)-2-((1R,3S,4S)-2-azabicyclo[2.2.1] heptan-3-yl)-1H-benzo[d]imidazole (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate (30 g) were suspended in 1, 4 dioxane (180 ml) and treated with hydrochloric acid (30 ml) at room temperature. The reaction mixture temperature may be raised to 70-75° C. and maintained for 1-2 hours. After completion of the reaction (checked by TLC), the reaction mass may be cooled to 25-30° C. The resultant solid was filtered and washed with 1, 4-dioxane. The obtained wet solid was suspended with purified water (100 ml) and its pH may be adjusted to 8-9 with 5% sodium carbonate solution under stirring conditions, and maintained for 30 minutes. The resulting slurry was filtered and dried under vacuum to obtain the objective compound with a yield of 22-25 g.

Example-7: Preparation of 6-(7-(2-((S)-5-azaspiro [2.4]heptan-6-yl)-1H-imidazol-5-yl)-9,9-difluoro-9H-fluoren-2-yl)-2-((1R,3S,4S)-2-azabicyclo[2.2.1] heptan-3-yl)-1H-benzo[d]imidazole (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate (30 g) were suspended in ethyl acetate (180 ml) and treated with hydrochloric acid (30 ml) at room temperature. The reaction mixture temperature may be raised to 70-75° C. and maintained for 1-2 hours. After completion of the reaction (checked by TLC), the reaction mass may be cooled to

23

25-30° C. The resultant solid was filtered and washed with ethyl acetate. The obtained wet solid may be suspended with purified water (100 ml) and its pH may be adjusted to 8-9 with 5% sodium carbonate solution under stirring conditions, and maintained for 30 minutes. The resulting slurry was filtered and dried under vacuum to obtain the objective compound with a yield of 22-25 g.

Example-8: Preparation of methyl[(2S)-1-{(6S)-6-[5-(9,9-difluoro-7-{2-[(1R,3S,4S)-2-{(2S)-2-[(methoxycarbonyl)amino]-3-methylbutanoyl}-2-azabicyclo[2.2.1]hept-3-yl]-1H-benzimidazol-6-yl}-9H-fluoren-2-yl)-1H-imidazol-2-yl]-5-azaspiro[2.4]hept-5-yl}-3-methyl-1-oxobutan-2-yl]carbamate propan-2-one [Ledipasvir Acetone solvate]

Methoxycarbonyl L-valine (11.25 g), hydroxybenzotriazole (9.25 g), 1-(3-dimethylaminopropyl)-3-ethylcarbodiimide hydrochloride (6.25 g), and dichloromethane (250 ml) were added to a flask. The reaction mixture may be agitated for 20 minutes at 23° C., and the solution may be cooled to 0-5° C. 6-(7-(2-((S)-5-azaspiro[2.4]heptan-6-yl)-1H-imidazol-5-yl)-9,9-difluoro-9H-fluoren-2-yl)-2-((1R,3S,4 S)-2-azabicyclo[2.2.1]heptan-3-yl)-1H-benzo[d]imidazole (25 g) and diisopropylethylamine (20 g) may be added to the reaction mixture and the contents may be stirred at 0-5° C. for 4 hours. After completion of the reaction, water may be added to the reaction mass and separated into two layers. The organic layer was washed with sodium bicarbonate and water. The organic layer may be distilled to half of the volume and cooled. Acetone may be added to the organic layer. The reaction contents may be seeded with Ledipasvir (acetone as a solvate) and stirred for 4 hours. The contents were filtered and washed with acetone and the cake may be dried to Ledipasvir acetone as a solvate (20-25 g).

Example-9: Preparation of methyl[(2S)-1-{(6S)-6-[5-(9,9-difluoro-7-{2-[(1R,3S,4S)-2-{(2S)-2-[(methoxycarbonyl)amino]-3-methylbutanoyl}-2-azabicyclo[2.2.1]hept-3-yl]-1H-benz imidazol-6-yl}-9H-fluoren-2-yl)-1H-imidazol-2-yl]-5-azaspiro[2.4]hept-5-yl}-3-methyl-1-oxobutan-2-yl]carbamate propan-2-one [Ledipasvir Acetone solvate]

Methoxycarbonyl L-valine (11.25 g) may be suspended in toluene (250 ml) to produce a clear solution and cooled to 0-5° C. Then the following may be added to the cold solution: hydroxybenzotriazole (9.25 g), 1-(3-dimethylaminopropyl)-3-ethylcarbodiimide hydrochloride (6.25 g), 6-(7-(2-((S)-5-azaspiro[2.4]heptan-6-yl)-1H-imidazol-5-yl)-9,9-difluoro-9H-fluoren-2-yl)-2-((1R,3S,4S)-2-azabicyclo[2.2.1]heptan-3-yl)-1H-benzo[d]imidazole (25 g), and diisopropylethylamine (20 g). After the reaction goes to completion, water may be added to the reaction mass and separated into two layers. The organic layer was washed with sodium bicarbonate and water. The organic layer was distilled under reduced pressure to produce a residue which may be dissolved in acetone (15 ml) to isolate Ledipasvir acetone solvate.

Example-10: Preparation of methyl[(2S)-1-{(6S)-6-[5-(9,9-difluoro-7-{2-[(1R,3S,4S)-2-{(2S)-2-[(methoxycarbonyl)amino]-3-methylbutanoyl}-2-azabicyclo[2.2.1]hept-3-yl]-1H-benzimidazol-6-yl}-9H-fluoren-2-yl)-1H-imidazol-2-yl]-5-azaspiro[2.4]hept-5-yl}-3-methyl-1-oxobutan-2-yl]carbamate propan-2-one [Ledipasvir Amorphous]

Ledipasvir acetone solvate (100 g) may be suspended in methanol (500 ml) at 0-5° C. and stirred for 10 minutes to produce a clear solution. Norit activated carbon (5 g) may be added to the clear solution and stirred at 0-5° C. for 20-30 minutes. The reaction mass may be filtered through a high flow bed and the obtained filtrate were added to pre-chilled purified water (500 ml) and stirred for 60-90 minutes at 0-5° C. The resultant solid was filtered, washed with water and dried at 70-80° C. to obtain 80-88 g of Ledipasvir in amorphous form.

Example-11: Preparation of methyl[(2S)-1-{(6S)-6-[5-(9,9-difluoro-7-{2-[(1R,3S,4S)-2-{(2S)-2-[(methoxycarbonyl)amino]-3-methylbutanoyl}-2-azabicyclo[2.2.1]hept-3-yl]-1H-benzimidazol-6-yl}-9H-fluoren-2-yl)-1H-imidazol-2-yl]-5-azaspiro[2.4]hept-5-yl}-3-methyl-1-oxobutan-2-yl]carbamate propan-2-one [Ledipasvir Amorphous]

Ledipasvir acetone solvate (100 g) may be suspended in tetrahydrofuran (500 ml) at 0-5° C. and stirred for 10 minutes to produce a clear solution. Norit activated carbon (5 g) was added to the clear solution and stirred at 0-5° C. for 20-30 minutes. The reaction mass may be filtered through a high flow bed and the obtained filtrate was added to pre-chilled purified water (500 ml) and stirred for 60-90 minutes at 0-5° C. The resultant solid was filtered, washed with water, and dried at 70-80° C. to obtain 80-88 g of Ledipasvir in amorphous form.

It will be apparent to those skilled in the art that the above methods and apparatuses may be changed or modified without departing from the general scope of the invention. The invention is intended to include all such modifications and alterations insofar as they come within the scope of the appended claims or the equivalents thereof.

We claim:

1. A process for the preparation of the acetone solvate of Ledipasvir and its salts of formula (I) comprising the steps of:

(a) reacting a suspension of (1R,3S,4S)-3-(6-bromo-1H-benzimidazol-2-yl)-2-azabicyclo[2.2.1]heptane-2-carboxylic acid 1,1-dimethylethyl ester of formula (X) in 1,4-dioxane with bis(pinacolato)diboron of formula (XI) in the presence of dichlorobis (di-tert-butylphenylphosphine) palladium (II) and potassium acetate at a temperature of 80-85° C. for 2 to 3 hours to produce (1R,3S,4S)-3-[6-(4,4,5,5-tetramethyl-1,3,2-dioxaborolan-2-yl)-1H-benzimidazol-2-yl]-2-azabicyclo[2.2.1]heptane-2-carboxylic acid 1,1-dimethylethyl ester (VIII),

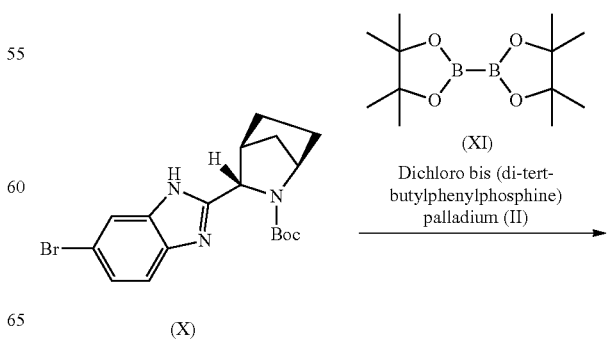

-continued

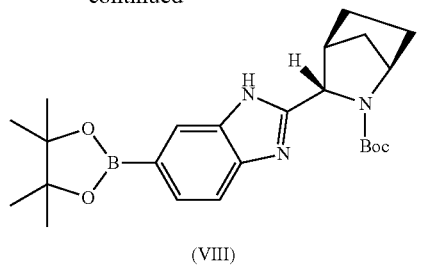

(VIII)

(b) condensing (1R,3S,4S)-3-[6-(4,4,5,5-tetramethyl-1,3,2-dioxaborolan-2-yl)-1H-benzimidazol-2-yl]-2-azabicyclo[2.2.1]heptane-2-carboxylic acid 1,1-dimethylethyl ester of formula (VIII) with (6S)-6-[5-(7-Bromo-9,9-difluoro-9H-fluoren-2-yl)-1H-imidazol-2-yl]-5-azaspiro[2.4]heptane-5-carboxylic acid 1,1-dimethylethyl ester of formula (V) in the presence of 1,4-dioxane, water, dimethyl formamide, dichlorobis-triphenylphosphene palladium (II), sodium carbonate and triphenyl phosphine (TPP) under an argon atmosphere at a temperature of 80-85° C. for 1 to 3 hours, to produce (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III),

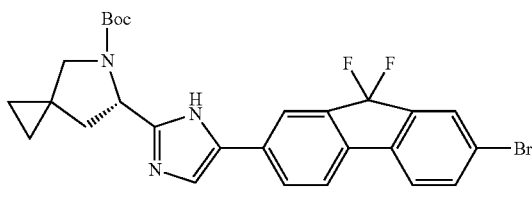

(V)

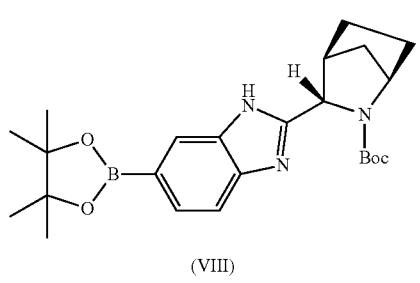

(VIII)

Dichloro bis triphenyl phosphene palladium (II)/
Sodium carbonate/Triphenyl phosphine (TPP)

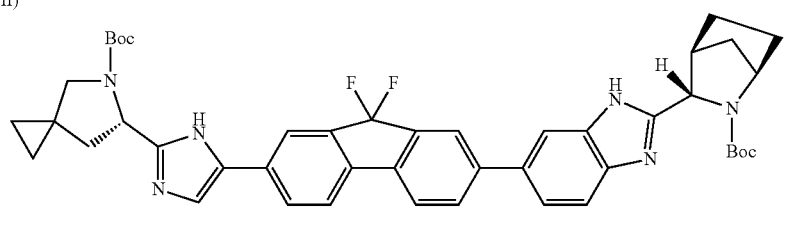

(III)

(c) deprotecting a suspension of (1R,3S,4S)-tert-butyl 3-(6-(7-(2-((S)-5-(tert-butoxy carbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III) in 1,4-dioxane or ethyl acetate by treatment with hydrochloric acid at 70-75° C. for 1 to 2 hours to produce 6-(7-(2-((S)-5-azaspiro[2.4]heptan-6-yl)-1H-imidazol-5-yl)-9,9-difluoro-9H-fluoren-2-yl)-2-((1R,3S,4S)-2-azabicyclo[2.2.1]heptan-3-yl)-1H-benzo[d]imidazole, free base of formula (IV); and

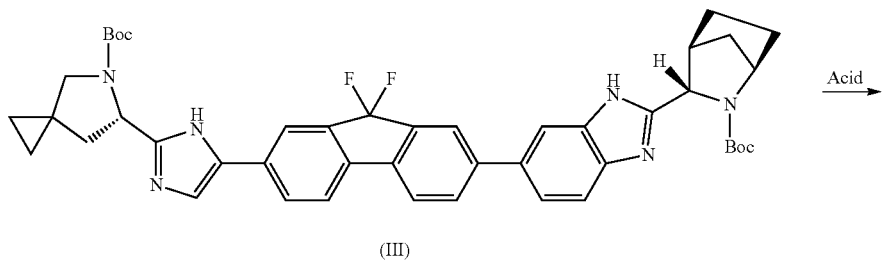

(III)

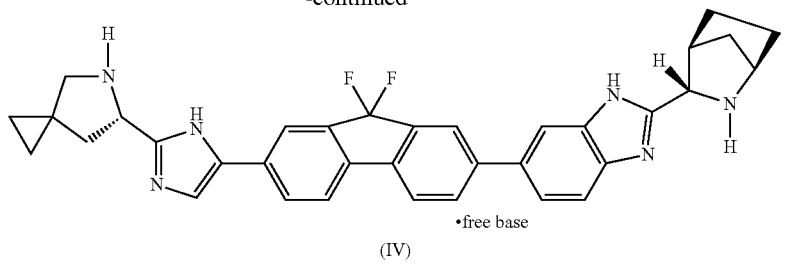

(IV) •free base (d) coupling of compound of formula (IV) with methoxy carbonyl L-valine of formula (VI) in the presence of hydroxybenzotriazole (HOBT), 1-(3-dimethylaminopropyl)-3-ethylcarbodiimide hydrochloride (EDC HCl) diisopropyl ethyl amine and dichloromethane or toluene as solvent at 0-5° C. for about 4 hours, separation of the organic layer by addition of water, partially or completely evaporating the organic layer, mixing the partially evaporated organic layer or the residue of complete evaporation with acetone and seeding the acetone solution with acetone solvate of Ledipasvir to produce the acetone solvate of Ledipasvir of formula (I)

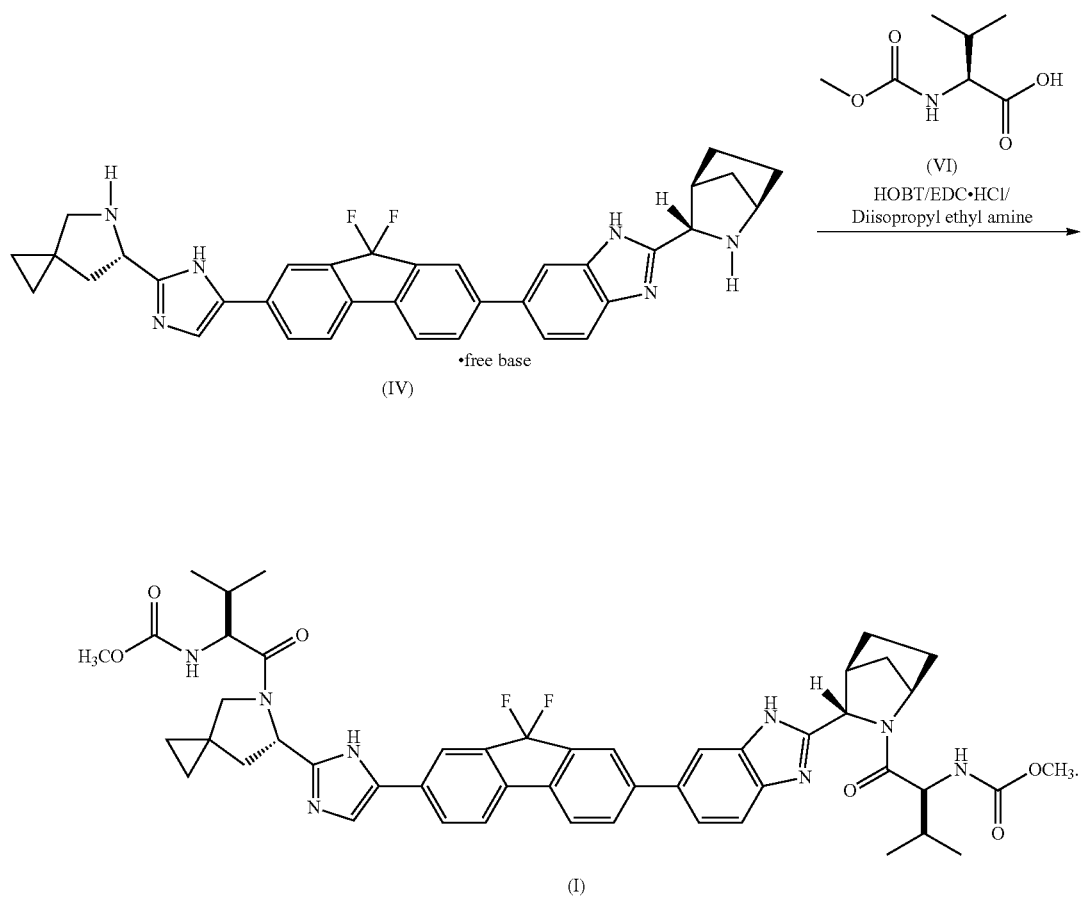

2. A process for the preparation of the acetone solvate of Ledipasvir of formula (I) comprising the steps of:

(a) reacting a suspension of (1R,3S,4S)-3-(6-bromo-1H-benzimidazol-2-yl)-2-azabicyclo[2.2.1]heptane-2-carboxylic acid 1,1-dimethylethyl ester of formula (X) in dimethyl formamide with bis(pinacolato)diboron of formula (XI) in the presence of dichlorobis (di-tert-butylphenylphosphine) nickel (II) and sodium acetate at a temperature of 80-85° C. for 2 to 3 hours to produce (1R,3S,4S)-3-[6-(4,4,5,5-tetramethyl-1,3,2-dioxaborolan-2-yl)-1H-benzimidazol-2-yl]-2-azabicyclo[2.2.1]heptane-2-carboxylic acid 1,1-dimethylethyl ester (VIII);

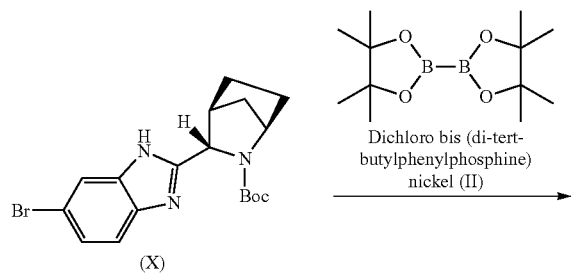

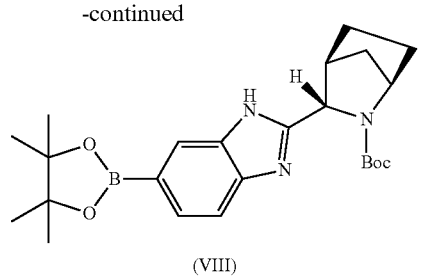

(VIII)

(b) condensing (1R,3S,4S)-3-[6-(4,4,5,5-tetramethyl-1,3,2-dioxaborolan-2-yl)-1H-benzimidazol-2-yl]-2-azabicyclo[2.2.1]heptane-2-carboxylic acid 1,1-dimethylethyl ester of formula (VIII) with (6S)-6-[5-(7-Bromo-9,9-difluoro-9H-fluoren-2-yl)-1H-imidazol-2-yl]-5-azaspiro[2.4]heptane-5-carboxylic acid 1,1-dimethylethyl ester of formula (V) in the presence of 1,4-dioxane, water, dimethyl formamide, dichlorobistriphenylphosphene nickel (II), sodium carbonate and triphenyl phosphine (TPP) under an argon atmosphere at a temperature of 80-85° C. for 1 to 3 hours to produce (1R,3S,4S)-tert-butyl 3-(6-(7-(2-((S)-5-(tert-butoxycarbonyl)-5-azaspiro[2.4]heptan-6-yl)-1H-imidazol-5-yl)-9,9-difluoro-9H-fluoren-2-yl)-1H-benzo[d]imidazol-2-yl)-2-azabicyclo[2.2.1]heptane-2-carboxylate of formula (III);

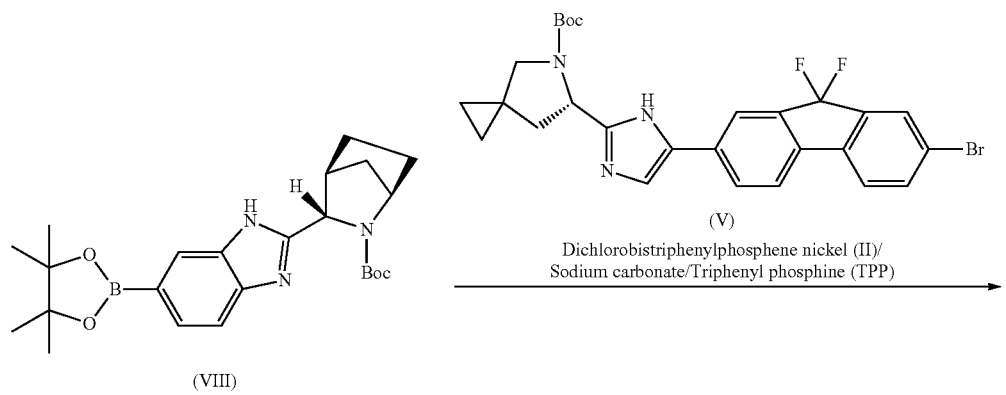

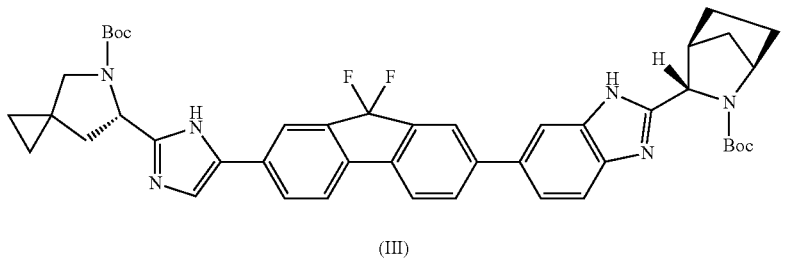

(III)

(c) deprotecting a suspension of (1R,3S,4S)-tert-butyl 3-(6-(7-(2-((S)-5-(tert-butoxy carbonyl)-5-azaspiro [2.4]heptan-6-yl)-1H-imidazol-5-yl)-9,9-difluoro-9H-fluoren-2-yl)-1H-benzo[d]imidazol-2-yl)-2-azabicyclo [2.2.1]heptane-2-carboxylate of formula (III) in 1,4-dioxane or ethyl acetate by treatment with hydrochloric acid at 70-75° C. for 1 to 2 hours to produce 6-(7-(2-((S)-5-azaspiro[2.4]heptan-6-yl)-1H-imidazol-5-yl)-9,9-difluoro-9H-fluoren-2-yl)-2-((1R,3S,4S)-2-azabicyclo[2.2.1]heptan-3-yl)-1H-benzo[d]imidazole, free base of formula (IV); and

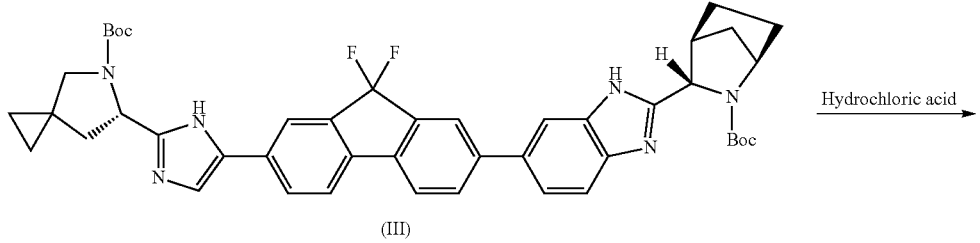

(III)

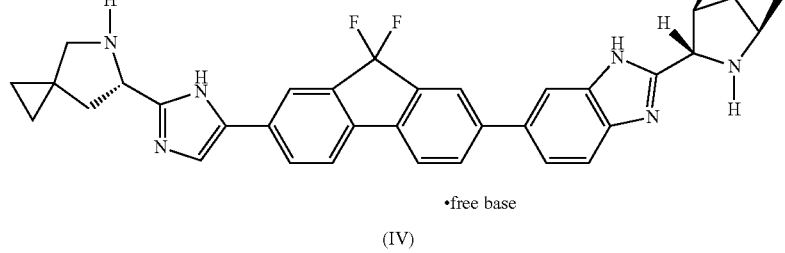

•free base
(IV)

(d) coupling of compound of formula (IV) with methoxy carbonyl L-valine of formula (VI) in the presence of hydroxybenzotriazole (HOBT), 1-(3-dimethylaminopropyl)-3-ethylcarbodiimide hydrochloride (EDC.HCl), diisopropyl ethyl amine and dichloromethane or toluene as solvent at 0-5° C. for about 4 hours, separation of the organic layer by addition of water, partially or completely evaporating the organic layer, mixing the partially evaporated organic layer or the residue of complete evaporation with acetone and seeding the acetone solution with acetone solvate of Ledipasvir to produce the acetone solvate of Ledipasvir of formula (I)

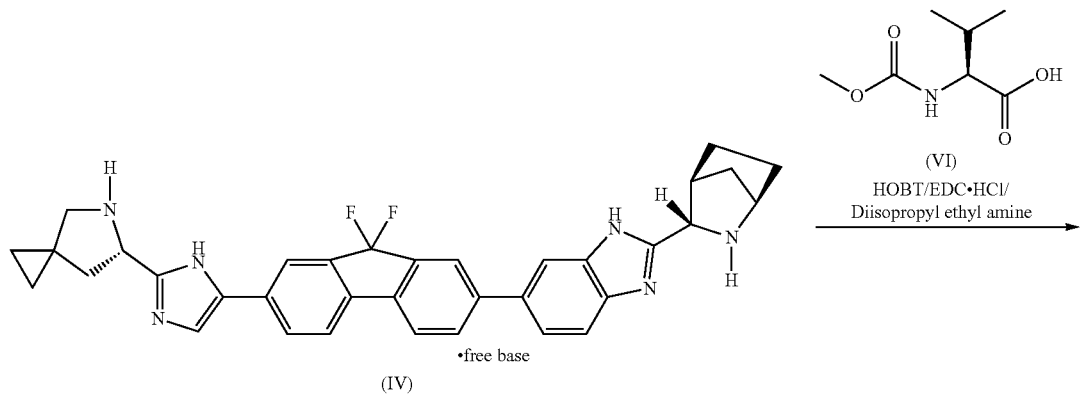

-continued
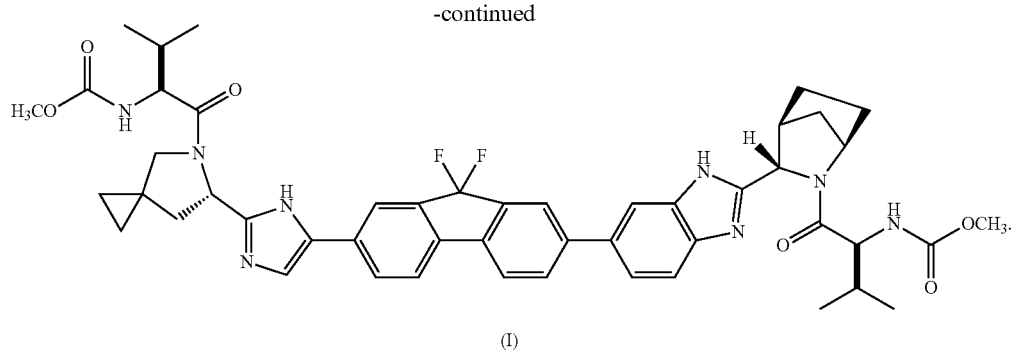
(I)